US009011659B2

(12) United States Patent
Grass

(10) Patent No.: US 9,011,659 B2
(45) Date of Patent: Apr. 21, 2015

(54) SENSOR APPARATUS FOR DETECTING A GAS CONCENTRATION AND A PARTICLE CONCENTRATION OF AN EXHAUST GAS

(75) Inventor: Philippe Grass, Regensburg (DE)

(73) Assignee: Continental Automotive GmbH, Hannover (DE)

( * ) Notice: Subject to any disclaimer, the term of this patent is extended or adjusted under 35 U.S.C. 154(b) by 0 days.

(21) Appl. No.: 14/110,339

(22) PCT Filed: Apr. 5, 2012

(86) PCT No.: PCT/EP2012/056256
§ 371 (c)(1),
(2), (4) Date: Oct. 7, 2013

(87) PCT Pub. No.: WO2012/136753
PCT Pub. Date: Oct. 11, 2012

(65) Prior Publication Data
US 2014/0034495 A1    Feb. 6, 2014

(30) Foreign Application Priority Data
Apr. 8, 2011    (DE) .................. 10 2011 016 490

(51) Int. Cl.
G01N 27/406   (2006.01)
G01N 27/419   (2006.01)
G01N 15/06    (2006.01)
F02D 41/22    (2006.01)
F02D 41/14    (2006.01)
F02M 25/07    (2006.01)

(52) U.S. Cl.
CPC ........ *G01N 27/4067* (2013.01); *G01N 15/0656* (2013.01); *G01N 27/419* (2013.01); *F02D 41/22* (2013.01); *F02D 41/1454* (2013.01); *F02D 41/1466* (2013.01); *F02M 25/0755* (2013.01)

(58) Field of Classification Search
CPC ............ G01N 15/0656; G01N 27/406; G01N 27/419; F02D 41/1466; F02D 41/22; F02D 41/1454; F02M 25/0755
USPC ........... 204/421–429; 73/23.31, 23.32, 28.01; 324/693
See application file for complete search history.

(56) References Cited

U.S. PATENT DOCUMENTS 7,832,254 B2 * 11/2010 Guenschel et al. .......... 73/28.01
2004/0104114 A1    6/2004 Schulte et al.
2005/0043899 A1 *  2/2005 Strassner et al. ............. 702/24
2008/0047847 A1 *  2/2008 Schmidt et al. ............ 205/793

(Continued)

FOREIGN PATENT DOCUMENTS

DE    199 60 338 A1    7/2001
DE    103 22 427 A1    12/2004

(Continued)

Primary Examiner — Jennifer Dieterle
(74) Attorney, Agent, or Firm — Cozen O'Connor

(57) ABSTRACT

A sensor apparatus includes a first electrode and a second electrode at a predefined distance from one another. The sensor apparatus includes a substrate arranged in a predefined first region of the sensor carrier such that the first electrode and the second electrode are substantially electrically decoupled from one another if the outer side of the sensor carrier is substantially free of particles. A third electrode is coupled to a solid electrolyte that is additionally coupled to the second electrode. A diffusion barrier is coupled to the third electrode in a predefined third region and the exhaust gas is applied to the third electrode only in the third region via the diffusion barrier.

7 Claims, 1 Drawing Sheet

(56) References Cited

U.S. PATENT DOCUMENTS

| | | |
|---|---|---|
| 2009/0114539 A1 | 5/2009 | Ziegler et al. |
| 2009/0301180 A1 | 12/2009 | Reutiman et al. |
| 2010/0301871 A1* | 12/2010 | Biskupski .................... 324/464 |
| 2011/0015824 A1* | 1/2011 | Ante et al. ..................... 701/34 |

FOREIGN PATENT DOCUMENTS

| | | |
|---|---|---|
| DE | 10 2005 049 775 A1 | 4/2007 |
| DE | 10 2006 048 354 A1 | 4/2008 |
| DE | 10 2006 048354 A1 | 4/2008 |
| JP | 3104291 B2 | 10/2000 |

\* cited by examiner

SENSOR APPARATUS FOR DETECTING A GAS CONCENTRATION AND A PARTICLE CONCENTRATION OF AN EXHAUST GAS

CROSS-REFERENCE TO RELATED APPLICATIONS

This is a U.S. national stage of application No. PCT/EP2012/056256, filed on 5 Apr. 2012, which claims priority to the German Application No.: 10 2011 016 490.1, filed: 8 Apr. 2011, the content of both incorporated herein by reference.

BACKGROUND OF THE INVENTION

1. Field of the Invention

The invention relates to a sensor apparatus for detecting a concentration of at least one gas component and a particle concentration of an exhaust gas. The sensor apparatus has a sensor carrier having a solid electrolyte.

2. Prior Art

Increasingly stringent statutory regulations require a reduction in the combustion exhaust gases emitted by a motor vehicle. In this connection, motor vehicles are increasingly being equipped with exhaust gas cleaning systems. A large number of sensors is required in order to monitor and/or control an exhaust gas cleaning apparatus of this kind.

DE 10 2006 048 354 A1 discloses a sensor element for identifying constituent parts of a gas mixture, in particular of an exhaust gas from internal combustion engines. The sensor element comprises a plurality of oxygen-ion-conducting solid electrolyte layers. Furthermore, the sensor element has a large number of electrically insulating ceramic layers. The sensor element furthermore has a ceramic heating element which is designed in the form of an electrical resistance conductor track and serves to heat up the sensor element, in particular to the temperature of the gas mixture which is to be determined, and/or to burn off the soot particles which have accumulated on large areas of the sensor element. Two measurement electrodes are fitted to a large area of the sensor element, said measurement electrodes preferably being in the form of interlocking interdigital electrodes. A reference gas channel which is preferably in contact with a reference gas atmosphere, such as air or oxygen for example, is arranged in one of the solid electrolyte layers. A reference electrode is arranged in the reference gas channel.

DE 103 22 427 A1 discloses a sensor for detecting particles in a gas stream, in particular soot particles in an exhaust gas stream, having measurement electrodes which are arranged on a substrate which is composed of an insulating material. The substrate comprises a solid electrolyte in which at least two oxygen pump cells, which each have an associated pair of electrodes, are formed. A diffusion barrier is connected upstream of at least one of the oxygen pump cells, said diffusion barrier having two further associated electrodes to which a high voltage can be applied.

DE 10 2005 049 775 A1 discloses a sensor for measuring the concentration of a gas component in a gas mixture. The sensor comprises an ion-conducting solid electrolyte. The sensor further comprises electrodes which are separated from one another by the solid electrolyte. From amongst the electrodes, an outer electrode is exposed to the gas mixture and an inner electrode is arranged in a cavity which is separated from the gas mixture by a diffusion barrier. The outer electrode consists of a solid body which leads to the formation of mixed potentials.

SUMMARY OF THE INVENTION

It is an object of the invention to provide a sensor apparatus which allows constituent parts of a gas mixture to be reliably identified.

In accordance with an aspect of the present invention, this object is achieved by a sensor apparatus for detecting a concentration of at least one gas component and a particle concentration of an exhaust gas in an exhaust gas channel of an internal combustion engine. The sensor apparatus has a sensor carrier having a solid electrolyte. The sensor apparatus further comprises a first electrode and a second electrode that are arranged at a prespecified distance from one another on an outer side of the sensor carrier. The sensor apparatus further comprises a substrate which has substantially no electrical conductivity at least below a prespecified operating limit temperature of the substrate and is arranged in a prespecified first region of the sensor carrier such that the first electrode and the second electrode are substantially electrically decoupled from one another if the outer side of the sensor carrier is substantially free of particles. The sensor apparatus has a third electrode that is coupled to the solid electrolyte, wherein the solid electrolyte is designed such that it is additionally coupled to the second electrode. The sensor apparatus further comprises a diffusion barrier that is arranged and designed in such a way that it is coupled to the third electrode in a prespecified third region and the exhaust gas from the exhaust gas channel is applied to the third electrode only in the third region via the diffusion barrier.

In one aspect, the solid electrolyte is, in particular, mechanically coupled to the second electrode and the third electrode. The solid electrolyte is preferably designed in such a way that it can electrolytically transport oxygen ions in a specific operating temperature range. Different concentrations of a gas mixture can advantageously be detected by the sensor apparatus. In this case, the first electrode and the second electrode can preferably be used to detect the particle concentration of the exhaust gas in the exhaust gas channel. The second electrode and the third electrode can be used to detect the concentration of the at least one gas component of the exhaust gas, for example an oxygen concentration of the exhaust gas. The particle concentration and the concentration of the at least one gas component can be detected by the sensor apparatus at different times. The sensor apparatus can be used, for example, for an on-board diagnosis system. For on-board diagnosis, it may be sufficient when, for example, a measurement signal from a lambda probe is only temporarily available and/or a measurement signal from a soot particle sensor is only temporarily available. The electrodes of the sensor apparatus can be actuated, for example, by means of a suitably designed control unit in such a way that the particle concentration can be detected at least once and the concentration of the gas mixture can be detected at least once in each case during a prespecified driving cycle. The driving cycle can be characterized, for example, by a prespecified time period, for example 500 s, and a prespecified operating state during the time period, for example cold starting of the internal combustion engine.

In another aspect, the sensor apparatus according to the invention can make a contribution to increasing the service life and the reliability of the sensor apparatus since the sensor apparatus allows a layer construction without cavities and/or without gas inflow channels. In the case of a sensor element in which the exhaust gas from the exhaust gas channel is applied to the second electrode via a gas inlet boundary with a cavity and/or a gas inflow channel, a condensate, for example, can enter the cavity and/or the gas inflow channel. Since the sensor apparatus is subjected to high temperature fluctuations, thermomechanical stresses can be produced, for example in the solid electrolyte which surrounds the respective cavity. The thermomechanical stresses can lead to damage to the sensor apparatus. The sensor apparatus can be produced in a cost-effective manner on account of the simple mechanical design.

In one aspect, the diffusion barrier has a porous ceramic material.

In another aspect, the substrate has the porous ceramic material and the diffusion barrier comprises the substrate. The diffusion barrier is arranged in the prespecified region of the sensor carrier such that it substantially electrically insulates the first electrode and the second electrode from one another if the outer side of the sensor carrier is substantially free of particles. This allows the sensor apparatus to be produced in a very simple and therefore cost-effective manner. Furthermore, the installation space for the sensor apparatus can be very low.

In a further aspect, the first electrode and the second electrode have an interdigital structure. This can make a contribution to the ability to detect a change in resistance and/or impedance between the first electrode and the second electrode in a very precise manner and therefore to ascertain the particle concentration in a very precise manner.

In a further aspect, the sensor apparatus has a heating element which is thermally coupled to the first electrode and the second electrode and the solid electrolyte. The heating element can advantageously be used to heat the solid electrolyte and to burn off particles which have accumulated on and/or between the first electrode and the second electrode. In particular, the heating element can be used to at least sometimes simultaneously heat the solid electrolyte and burn off particles. The solid electrolyte has an ion conductivity only starting from a prespecified operating temperature of the solid electrolyte. For example, zirconium oxide has ion conductivity only at a minimum operating temperature of approximately >450° C. Therefore, the solid electrolyte sensor is preferably heated in an arrangement of a solid electrolyte sensor in an exhaust gas duct of an internal combustion engine in an installation position in which the exhaust gas is at a lower temperature than the minimum operating temperature. The heating element can further be used to burn the particles which have collected on the sensor apparatus, in particular the particles that have accumulated on and/or between the first electrode and the second electrode, and therefore to regenerate the sensor apparatus. The heating element is preferably actuated in this way when a limit thickness of a particle layer on and/or between the first electrode and the second electrode is reached or exceeded. In order to burn the particles, it is necessary to heat the sensor apparatus in an electrode region that comprises the first electrode, the second electrode and the region between the first electrode and the second electrode. In order to burn the particles, it is necessary to heat this electrode region to, for example, 800° C.

In a further aspect, the second electrode and the third electrode are arranged on the same first side of the solid electrolyte. This allows the sensor apparatus to be produced in a cost-effective manner. In this case, the sensor apparatus can have, for example, a planar layer structure or a circular-cylindrical layer structure.

In another aspect, the second electrode and the third electrode are at a prespecified distance from one another along a first axis, and are at least partially embedded in the solid electrolyte in a manner vertically offset in relation to one another along a second axis that is orthogonal to the first axis.

The at least partial embedding of the second electrode and the third electrode can also comprise the second electrode and/or the third electrode lying on the solid electrolyte.

In another aspect, the heating element is arranged in the sensor carrier on a second side that is averted from the first side of the solid electrolyte.

In another aspect, the second electrode and the third electrode have a porous platinum alloy.

BRIEF DESCRIPTION OF DRAWINGS

Exemplary embodiments of the invention are explained below with reference to the schematic drawings, in which.

Elements with the same structure or function are provided with the same reference symbols throughout the figures.

DETAILED DESCRIPTION OF THE PRESENTLY PREFERRED EMBODIMENTS

Figure 1:
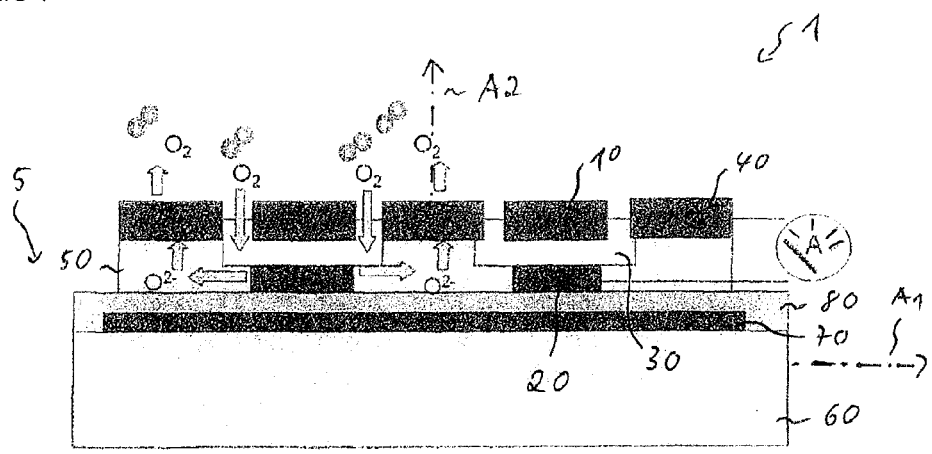
FIG. 1 is a cross-sectional view through an exemplary embodiment of a sensor apparatus for detecting a concentration of at least one gas component and a particle concentration of an exhaust gas.

The sensor apparatus 1 can be arranged, for example, at least partially in an exhaust gas channel of an internal combustion engine of a motor vehicle at one or more points, for example downstream of a particulate filter of the motor vehicle. The motor vehicle can be, for example, a diesel motor vehicle. The sensor apparatus 1 can be used, for example, to ascertain an oxygen concentration and a soot particle concentration in the exhaust gas channel. As an alternative or in addition, the sensor apparatus 1 can be arranged at least partially in an exhaust gas return channel of an internal combustion engine. The sensor apparatus 1 can preferably be used in an environment with an oxygen concentration of approximately >2%, in particular >5%.

The sensor apparatus 1 has a sensor carrier 5 with a solid electrolyte 50. The solid electrolyte 50 can comprise, for example, a plurality of oxygen-conducting solid electrolyte layers. The solid electrolyte 50 can have, for example, yttrium-stabilized zirconium dioxide (YSZ). Further, the sensor carrier 5 can have, for example, one or more electrically insulating, thermally conductive layers that comprise a ceramic material.

The sensor apparatus 1 further comprises a first electrode 10 and a second electrode 40, which are arranged at a prespecified distance from one another on an outer side of the sensor carrier 5. The sensor apparatus 1 is preferably oriented in the exhaust gas channel in such a way that the first electrode 10 and the second electrode 40 face the exhaust gas stream. However, a different orientation of the sensor apparatus 1 in the exhaust gas channel is also possible in principle.

The sensor apparatus 1 has a third electrode 20 that is coupled to the solid electrolyte 50. The solid electrolyte 50 is designed such that it is additionally coupled to the second electrode 40. In the sensor apparatus 1 shown in FIG. 1, the third electrode 20 and the second electrode 40 are arranged on the same side of the solid electrolyte 50. The sensor apparatus 1 can have, for example, a planar layer structure. The third electrode 20 and the second electrode 40 are at a prespecified distance from one another along a first axis A1 and are at least partially embedded in the solid electrolyte 50 in a manner vertically offset in relation to one another along a second axis A2, which is orthogonal to the first axis A1.

The second electrode 20 and the third electrode 40 can have, for example, a porous platinum alloy. As an alternative, the second electrode and the third electrode can have another porous metal alloy. The first electrode 10 can have the porous platinum alloy or another porous metal alloy. As an alternative, the first electrode can have a platinum alloy or another metal alloy with no or substantially no porosity.

The sensor apparatus 1 can have, for example, a carrier 60 and a heating element 70. By way of example, a heating insulation means 80, which comprises, for example, at least one of the electrically insulating, thermally conductive layers, can be arranged between the heating element 70 and the solid electrolyte 50.

The sensor apparatus 1 further comprises a substrate that has substantially no electrical conductivity at least below a prespecified operating limit temperature of the substrate and is arranged in a prespecified first region of the sensor carrier 5 such that the first electrode 10 and the second electrode 40 are substantially electrically decoupled from one another if the outer side of the sensor carrier 5 is substantially free of particles. The sensor apparatus 1 further comprises a diffusion barrier 30. The diffusion barrier 30 is arranged and designed in such a way that it is coupled to the third electrode in a prespecified third region, and the gas mixture from the gas space is applied to the third electrode 20 only in the third region via the diffusion barrier 30. In the exemplary embodiment shown in FIG. 1, the diffusion barrier 30 comprises the substrate and the diffusion barrier 30 is arranged in the prespecified region of the sensor carrier 5 such that it substantially electrically insulates the first electrode 10 and the second electrode 40 from one another if the outer side of the sensor carrier 5 is substantially free of particles. The first electrode 10 is arranged such that it is, for example, partially embedded in the diffusion barrier 30. The substrate has, for example, a porous ceramic material with a high level of thermal conductivity, with the result that the heating element 70 is thermally coupled to the first electrode 10 and the second electrode 40 and the solid electrolyte 50.

Figure 2:
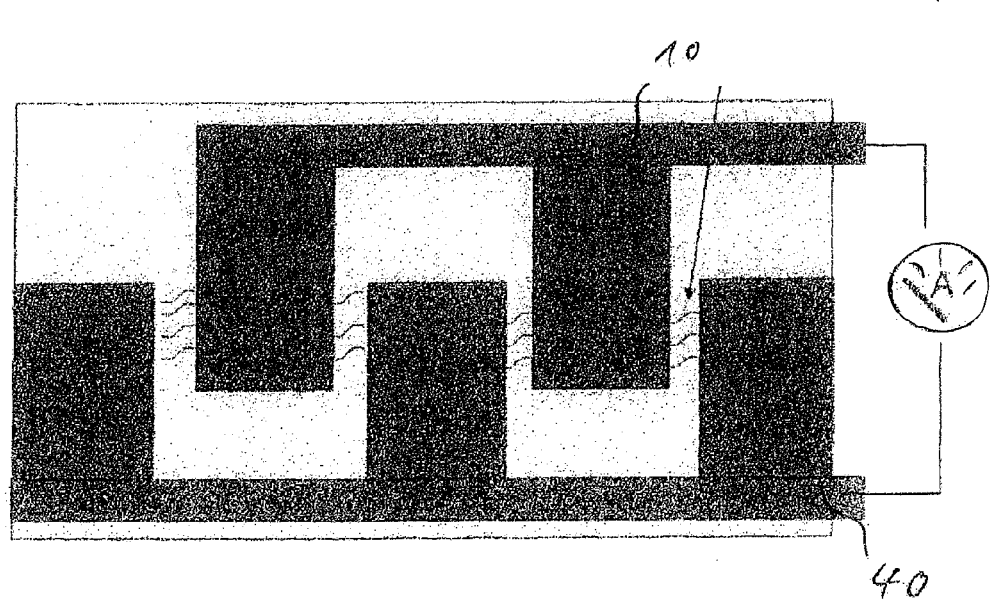
FIG. 2 is a plan view of the sensor apparatus.

FIG. 2 shows a plan view of the sensor apparatus 1. The first electrode 10 and the second electrode 40 have an interdigital structure.

Preferably, the particle concentration is ascertained as a function of a detected change in resistance and/or impedance between the first electrode 10 and the second electrode 40 during a first time period, and the concentration of the at least one gas component is ascertained as a function of a detected pump current, which flows between the second electrode and the third electrode, during a second time period in each case at different times during an operating period of the sensor apparatus 1.

During the first time period, a prespecified voltage can be applied to the first electrode 10 and the second electrode 40, for example, by means of a suitably designed sensor measurement unit, with the result that particles from the exhaust gas stream noticeably accumulate on and/or between the first electrode 10 and the second electrode 40. As the voltage is applied to the first electrode 10 and the second electrode 40, electrically charged particles, for example soot particles, are preferably attracted to and collect on and/or between the first electrode 10 and the second electrode 40. The sensor measurement unit can further be designed to detect a sensor current as a function of the voltage which is applied between the first electrode 10 and the second electrode 40 and the collected particles on and/or between the first electrode 10 and the second electrode 40 and to ascertain an electrical resistance between the first electrode 10 and the second electrode 40 as a function of the voltage and the sensor current. The electrical resistance between the first electrode 10 and the second electrode 40 preferably has a significantly higher resistance value in a regenerated, that is to say cleaned, sensor apparatus 1 than in a sensor apparatus 1 that has not been cleaned. If particles collect between the first electrode 10 and the second electrode 40, the value of the electrical resistance falls. The electrical resistance is therefore dependent on a thickness of a particle layer which has collected on and/or between the first electrode 10 and the second electrode 40.

In order to detect the concentration of the gas component in the exhaust gas, the third electrode 20 and the second electrode 40 of the sensor apparatus 1 can be electrically coupled to a current source. During the second time period, the current source can be actuated to the effect that it is disconnected during a measurement phase, and an electrode voltage between the third electrode and the second electrode 40 can be detected. Furthermore, a pump current can be ascertained as a function of a deviation in the electrode voltage from a prespecified setpoint voltage. During an operating phase of the second time period that follows the measurement phase, the current source can be actuated in such a way that it outputs the pump current to the second electrode 40 of the sensor element. The steps of the measurement phase and the subsequent actuation of the current source for outputting the pump current to the second electrode 40 are run through several times so as to minimize the deviation between the electrode voltage and the prespecified setpoint voltage. The concentration of the exhaust gas in the exhaust gas channel can be ascertained as a function of the pump current.

During a regeneration phase, the heating element 70 can be used to burn the particles that are collected on the sensor apparatus 1, in particular the particles that have accumulated on and/or between the first electrode 10 and the second electrode 40, thereby regenerating the sensor apparatus 1. The heating element 70 is preferably actuated to this effect when a particle layer on and/or between the first electrode 10 and second electrode 40 has reached or exceeded a limit thickness. The burn-off process can be performed in an intermediate phase which follows the first time period and precedes the second time period. In this case, it is sufficient when the solid electrolyte 50 is heated during the second time period in such a way that it is at least temporarily at a prespecified operating temperature that is greater than a minimum operating temperature at which the solid electrolyte 50 has the ion conductivity and which is lower than a burn-off temperature which is required for burning off the particles. In addition or as an alternative, it is possible for the heating element 70 to be operated during at least one of the operating phases within the second time period in such a way that the operating temperature of the solid electrolyte 50 is at a value above the minimum operating temperature and at the same time the soot particles can be burnt off from the first electrode 10 and the second electrode 40. The heating element 70 is preferably likewise actuated to the effect that it is disconnected during the respective measurement phase.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A sensor apparatus (1) for detecting a concentration of at least one gas component and a particle concentration of an exhaust gas in an exhaust gas channel of an internal combustion engine, the sensor apparatus comprising:
    a sensor carrier (5) having a solid electrolyte (50);
    a first electrode (10) and a second electrode (40), arranged at a prespecified distance from one another on an outer side of the sensor carrier (5),
    a substrate having substantially no electrical conductivity at least below a prespecified operating limit temperature of the substrate, the substrate being arranged in a prespecified first region of the sensor carrier (5) such that the first electrode (10) and the second electrode (40) are substantially electrically decoupled from one another if the outer side of the sensor carrier (5) is substantially free of particles; and
    a third electrode (20) coupled to the solid electrolyte (50), wherein the solid electrolyte (50) is additionally coupled to the second electrode (40),
    wherein the sensor apparatus has a diffusion barrier (30) arranged so as to be coupled to the third electrode (20) in a prespecified third region, and the exhaust gas from the exhaust gas channel is applied to the third electrode (20) only in the third region via the diffusion barrier (30),
    wherein the first electrode (10) and the second electrode (40) have an interdigital structure, and
    wherein the second electrode (40) and the third electrode (20) are separated at a prespecified distance from one another along a first axis (A1), and are at least partially embedded in the solid electrolyte (50) such that the second electrode (40) and the third electrode (20) are vertically offset in relation to one another along a second axis (A2) over an entirety of the apparatus, the second axis being orthogonal to the first axis (A1).

2. The sensor apparatus (1) as claimed in claim 1, wherein the diffusion barrier (30) has a porous ceramic material.

3. The sensor apparatus (1) as claimed in claim 2, wherein:
    the substrate has the porous ceramic material,
    the diffusion barrier (30) comprises the substrate, and
    the diffusion barrier (30) is arranged in the prespecified region of the sensor carrier (5) such that it substantially electrically insulates the first electrode (10) and the second electrode (40) from one another if the outer side of the sensor carrier (5) is substantially free of particles.

4. The sensor apparatus (1) as claimed in claim 1, the sensor apparatus further comprising a heating element (70) thermally coupled to the first electrode (10), the second electrode (40) and the solid electrolyte (50).

5. The sensor apparatus (1) as claimed in claim 4, wherein the second electrode (40) and the third electrode (20) are arranged on a first side of the solid electrolyte (50).

6. The sensor apparatus (1) as claimed in claim 5, wherein the heating element (70) is arranged in the sensor carrier (5) on a second side which is averted from the first side of the solid electrolyte (50).

7. The sensor apparatus (1) as claimed in claim 1, wherein the second electrode (20) and the third electrode (40) have a porous platinum alloy.

* * * * *